United States Patent
Korn et al.

(10) Patent No.: US 9,776,940 B2
(45) Date of Patent: Oct. 3, 2017

(54) PROCESS FOR PRODUCTION OF ACRYLIC ACID

(71) Applicant: BASF SE, Ludwigshafen (DE)

(72) Inventors: Tobias Korn, Goennheim (DE); Till Blum, Schifferstadt (DE); Travis Carline, Lake Jackson, TX (US); Christopher Fuchs, Angleton, TX (US); Darryl Welch, Lake Jackson, TX (US); Peter Zurowski, Landau (DE); Volker Schliephake, Schifferstadt (DE); Steffen Rissel, Kirchheim (DE); Thorsten Friese, Hong Kong (CN); Ulrich Jaeger, Roemerberg (DE); Sylke Haremza, Neckargemuend (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/227,392

(22) Filed: Aug. 3, 2016

(65) Prior Publication Data

US 2017/0036982 A1    Feb. 9, 2017

Related U.S. Application Data

(60) Provisional application No. 62/202,192, filed on Aug. 7, 2015.

(51) Int. Cl.
*C07C 51/43* (2006.01)
*C07C 45/32* (2006.01)
(Continued)

(52) U.S. Cl.
CPC .............. *C07C 45/32* (2013.01); *C07C 45/33* (2013.01); *C07C 45/35* (2013.01); *C07C 45/38* (2013.01);
(Continued)

(58) Field of Classification Search
CPC combination set(s) only.
See application file for complete search history.

(56) References Cited

U.S. PATENT DOCUMENTS

| 3,932,500 A | 1/1976 | Duembgen et al. |
| 4,110,370 A | 8/1978 | Engelbach et al. |

(Continued)

FOREIGN PATENT DOCUMENTS

| CA | 2259994 | 1/1998 |
| DE | 1 960 687 | 6/1971 |

(Continued)

OTHER PUBLICATIONS

International Search Report and Written Opinion of the International Searching Authority issued Sep. 14, 2016 in PCT/EP2016/068478 filed Aug. 3, 2016 (English translation only).

*Primary Examiner* — Jafar Parsa
*Assistant Examiner* — Amy C Bonaparte
(74) *Attorney, Agent, or Firm* — Oblon, McClelland, Maier & Neustadt, L.L.P.

(57) ABSTRACT

A process for production of acrylic acid includes preparing a product gas mixture by a catalytic gas-phase oxidation of a $C_3$ precursor; cooling and contacting the cooled product gas mixture in an absorption column having at least two cooling loops in countercurrent with an absorbent to obtain an absorbate A, containing the absorbent and absorbed acrylic acid; condensing a high boiler fraction of the product gas mixture in a first cooling loop; condensing a low boiler fraction of the product gas mixture in a second cooling loop; maintaining a temperature of the absorbate A in the second cooling loop at a value of at least 56° C.; removing an acid water stream comprising glyoxal from the absorption column at a side take-off located above the second cooling loop; and removing a stream F of absorbate A from the absorption (Continued)

column at a side take-off, located at a height of the absorption column between the first cooling loop and the second cooling loop.

15 Claims, 4 Drawing Sheets

(51) Int. Cl.
  *C07C 51/21* (2006.01)
  *C07C 51/245* (2006.01)
  *C07C 51/42* (2006.01)
  *C07C 45/78* (2006.01)
  *C07C 51/235* (2006.01)
  *C07C 51/25* (2006.01)
  *C07C 51/44* (2006.01)
  *C07C 45/35* (2006.01)
  *C07C 45/33* (2006.01)
  *C07C 45/39* (2006.01)
  *C07C 45/38* (2006.01)
  *C07C 57/04* (2006.01)
  *C07C 51/47* (2006.01)

(52) U.S. Cl.
  CPC ............ *C07C 45/39* (2013.01); *C07C 45/783* (2013.01); *C07C 51/21* (2013.01); *C07C 51/235* (2013.01); *C07C 51/245* (2013.01); *C07C 51/252* (2013.01); *C07C 51/42* (2013.01); *C07C 51/43* (2013.01); *C07C 51/44* (2013.01); *C07C 51/47* (2013.01); *C07C 57/04* (2013.01)

(56) References Cited

U.S. PATENT DOCUMENTS

| | | | |
|---|---|---|---|
| 5,108,578 | A | 4/1992 | Somes et al. |
| 5,426,221 | A | 6/1995 | Willersinn |
| 5,780,679 | A | 7/1998 | Egly et al. |
| 5,831,124 | A | 11/1998 | Machhammer et al. |
| 6,143,916 | A | 11/2000 | Hinago et al. |
| 6,806,385 | B1 | 10/2004 | Hammon et al. |
| 2004/0063988 | A1 | 4/2004 | Hechler et al. |
| 2004/0097368 | A1 | 5/2004 | Borgmeier et al. |
| 2004/0236049 | A1 | 11/2004 | Fuchs et al. |
| 2004/0242826 | A1 | 12/2004 | Nishimura |
| 2005/0119515 | A1 | 6/2005 | Machhammer et al. |
| 2007/0088092 | A1 | 4/2007 | Klanner et al. |
| 2010/0022734 | A1 | 1/2010 | Blum et al. |
| 2011/0036704 | A1 | 2/2011 | Blum et al. |
| 2012/0085969 | A1 | 4/2012 | Blum et al. |

FOREIGN PATENT DOCUMENTS

| | | |
|---|---|---|
| DE | 2 136 396 | 2/1973 |
| DE | 24 49 780 A1 | 4/1976 |
| DE | 43 08 087 A1 | 9/1994 |
| DE | 44 36 243 A1 | 4/1996 |
| DE | 196 06 877 A1 | 8/1997 |
| DE | 196 27 850 A1 | 1/1998 |
| DE | 198 35 247 A1 | 2/1999 |
| DE | 198 10 962 A1 | 9/1999 |
| DE | 101 31 297 A1 | 1/2003 |
| DE | 101 38 150 A1 | 2/2003 |
| DE | 102 51 138 A1 | 11/2003 |
| DE | 103 36 386 A1 | 3/2004 |
| DE | 102 45 585 A1 | 4/2004 |
| DE | 102 46 119 A1 | 4/2004 |
| DE | 10 2005 052 917 A1 | 10/2007 |
| DE | 10 2008 040 799 A1 | 12/2008 |
| DE | 10 2008 041 573 A1 | 3/2010 |
| EP | 0 117 146 A1 | 8/1984 |
| EP | 0 608 838 A2 | 8/1994 |
| EP | 0 722 926 A1 | 7/1996 |
| EP | 0 770 592 A1 | 5/1997 |
| EP | 0 925 272 | 6/1999 |
| EP | 0 990 636 A1 | 4/2000 |
| EP | 1 015 410 | 7/2000 |
| EP | 1 041 062 A2 | 10/2000 |
| EP | 1 272 453 A1 | 1/2003 |
| EP | 1 298 120 A2 | 4/2003 |
| EP | 1 396 484 A1 | 3/2004 |
| EP | 1 484 303 A2 | 12/2004 |
| EP | 1 484 308 A1 | 12/2004 |
| EP | 1 484 309 A1 | 12/2004 |
| WO | WO 97/48669 | 12/1997 |
| WO | WO 99/14181 | 3/1999 |
| WO | WO 01/77056 A1 | 10/2001 |
| WO | WO 01/96270 A2 | 12/2001 |
| WO | WO 01/96271 A2 | 12/2001 |
| WO | WO 02/055469 A1 | 7/2002 |
| WO | WO 03/011804 A2 | 2/2003 |
| WO | WO 03/078378 A1 | 9/2003 |
| WO | WO 2005/007609 A1 | 1/2005 |
| WO | WO 2005/042459 A1 | 5/2005 |
| WO | WO 2005/047224 A1 | 5/2005 |
| WO | WO 2005/047226 A1 | 5/2005 |
| WO | WO 2005/073160 A1 | 8/2005 |
| WO | WO 2005/113127 A1 | 12/2005 |
| WO | WO 2006/092272 A2 | 9/2006 |
| WO | WO 2006/114506 A1 | 11/2006 |
| WO | WO 2006/136336 A2 | 12/2006 |
| WO | WO 2007/076370 A2 | 7/2007 |
| WO | WO 2007/090991 A2 | 8/2007 |

PROCESS FOR PRODUCTION OF ACRYLIC ACID

The present invention relates to a process for production of acrylic acid comprising the steps of preparation of a product gas mixture, cooling of the product gas mixture, contacting the product gas mixture with an absorbent, wherein an absorbate A is formed, and introducing a feed stream F comprising at least part of the absorbate A into a rectification column.

Acrylic acid is an important monomer which finds use as such and/or in the form of its alkyl esters for production of polymers used in the hygiene sector, for example in water-superabsorbing polymers as described in for example, WO 02/055469 and WO 03/078378.

Acrylic acid can be prepared, for example, by heterogeneously catalyzed partial oxidation of a $C_3$ precursor compound such as propylene, propane, acrolein, propionaldehyde, propionic acid, propanol and/or glycerol in the gas phase, as disclosed in for example, EP-A 990 636, U.S. Pat. No. 5,108,578, EP-A 1 015 410, EP-A 1 484 303, EP-A 1 484 308, EP-A 1 484 309, US-A 2004/0242826 and WO 2006/136336.

In principle, in the course of such a heterogeneously catalyzed partial gas phase oxidation, pure acrylic acid is not obtained, but instead merely a product gas mixture which comprises acrylic acid and, in addition to acrylic acid, also comprises constituents other than acrylic acid, from which the acrylic acid has to be removed. Such a constituent other than acrylic acid in the product gas mixture will normally be steam. A reason for this is that steam firstly typically constitutes a by-product of the partial oxidation and secondly is regularly also used as an inert diluent gas in the partial oxidation reactions.

The nature and the particular proportion of the constituents other than acrylic acid in the product gas mixture of the partial oxidation of the $C_3$ precursor compound of acrylic acid can be influenced by parameters including the purity of the $C_3$ precursor compound used as the raw material and the reaction conditions, including the catalysts used, under which the heterogeneously catalyzed partial gas phase oxidation is performed like, for example in DE-A 101 31 297 and DE-A 10 2005 052 917. Typical of such secondary constituents other than acrylic acid and steam are, for example, carbon oxides, such as CO and $CO_2$, molecular nitrogen, molecular oxygen, low molecular weight alkanes such as propane, ethane and methane, lower saturated carboxylic acids such as formic acid, acetic acid and propionic acid, lower aldehydes such as formaldehyde, benzaldehyde and furfurals, and higher carboxylic acids or anhydrides thereof, such as benzoic acid, phthalic anhydride and maleic anhydride.

A portion of these secondary constituents other than acrylic acid and steam is, in its pure form at standard pressure of 1 bar, more volatile than pure acrylic acid, which corresponds to having a boiling point lower than that of acrylic acid at standard pressure. These secondary constituents are also referred to as low boilers when their boiling point at standard pressure is at least 0° C. and is at the same time at least 20° C. below the boiling point of acrylic acid at standard pressure. Acetic acid is an example for a low boiler.

When the boiling point of the aforementioned secondary constituents at standard pressure is less than 0° C., they can be encompassed under the term "uncondensables". The uncondensable secondary constituents include especially secondary constituents such as molecular nitrogen which are much more volatile than water.

Another portion of the secondary constituents is very much less volatile than acrylic acid, such as phthalic anhydride, and has a boiling point at standard pressure which is at least 75° C. above that of acrylic acid at standard pressure. These secondary constituents can be referred to as high boilers.

Secondary constituents such as maleic anhydride whose boiling points at standard pressure are less than 20° C. below and more than 75° C. above that at standard pressure of acrylic acid can be referred to as medium boilers.

For removal of acrylic acid from the product gas mixture of a heterogeneously catalyzed partial gas phase oxidation of at least one $C_3$ precursor compound, various processes are known in the prior art as described, for example, in documents DE-A 103 36 386, DE-A 196 27 850, DE-A 024 49 780 and EP-A 925 272.

In some processes the acrylic acid is removed from an absorbate comprising it in dissolved form essentially in a rectifying section of a rectification column in the form of a crude acrylic acid whose proportion by weight of acrylic acid is at least 90% by weight.

For numerous end uses, however, this purity of crude acrylic acid is insufficient as for example described in EP-A 770 592. While numerous prior art documents promote crystallizative further purification of crude acrylic acid for various reasons, for example EP-A 1 272 453, DE-A 196 06 877 and German application 10 2008 041 573.1, a rectificative further purification of crude acrylic acid to give pure acrylic acid is installed in many existing industrial scale production plants for reasons of historical process development, referring to for example DE-A 101 38 150.

It is already known from EP-A 770 592, that the product gas mixture of a heterogeneously catalyzed partial gas phase oxidation of at least one $C_3$ precursor compound to acrylic acid may comprise, among other constituents, various aldehydes as constituents other than acrylic acid. It is also known from EP-A 770 592 that very small amounts of aldehydic impurities present in acrylic acid significantly increase the tendency of acrylic acid to undesired free-radical polymerization. EP-A 770 592 and DE-A 101 38 150 therefore recommend adding aldehyde scavengers to the particular acrylic acid prior to the rectification thereof in the case of rectification of such an acrylic acid, for example a crude acrylic acid, comprising aldehydic impurities. However, the additional requirement therefore simultaneously accounts for the disadvantageousness of this process.

EP-A 1 298 120 discloses that a possible by-product of a heterogeneously catalyzed partial gas phase oxidation of $C_3$ precursors which can be formed under particular conditions is also the aldehyde glyoxal. For reasons including the fact that glyoxal promotes the undesired free-radical polymerization of acrylic acid, EP-A 1 298 120 recommends configuring the acrylic acid preparation such that the glyoxal by-product formation is minimized. One possible source for glyoxal by-product formation in the course of a heterogeneously catalyzed partial gas phase oxidation of $C_3$ precursors of acrylic acid stated by EP-A 1 298 120 is the $C_2$ impurity ethylene which is possibly present in the $C_3$ precursor. With additional use of reverse osmosis separation processes, according to EP-A 1 298 120, it is possible to obtain product gas mixtures from which the acrylic acid, even in the case of circulation of the absorbent, can be transferred to liquid phases which comprise less than 100 ppm by weight of glyoxal. According to the teaching of EP-A 1 298 120, the acrylic acid can subsequently be removed from such liquid phases in a comparatively problem-free manner by means of distillative separation processes. However, a disadvantage of this process is the requirement for reverse osmosis, which reduces the space-time yield.

DE-A 10 2008 040 799 discloses that the ability of glyoxal, as an impurity in acrylic acid, to promote the tendency of the acrylic acid to undesired free-radical polymerization, compared to other possible by-product aldehydes of a heterogeneously catalyzed partial gas phase oxidation of $C_3$ precursor compounds, for example acetaldehyde, formaldehyde, propionaldehyde, benzaldehyde, butyraldehyde, acrolein and furfural, based on equal molar impurity contents, is very much more marked. This is attributed in DE-A 10 2008 040 799 to the fact that the thermal expenditure for splitting of monomeric glyoxal into two formyl radicals is firstly particularly low, and the resulting formyl radicals are secondly particularly reactive.

EP-A 1 396 484 discloses a process, different than the method recommended in EP-A 1 298 120, for separating acrylic acid present as a main product and glyoxal present as a by-product in a product gas mixture of a partial heterogeneously catalyzed gas phase oxidation of a $C_3$ precursor compound of acrylic acid, which tolerates higher by-product contents of glyoxal. Among other reasons, this is advantageous in that it permits the use of economically more attractive $C_3$ precursor compounds having an increased impurity content.

In this process, the acrylic acid and the glyoxal are absorbed from the product gas mixture initially into an aqueous solution. The water is subsequently removed from this solution by azeotropic distillation or rectification. In order to substantially suppress undesired polymer formation, the process should be such that the reflux liquid has certain water contents and the reflux ratio does not go below a certain value. In addition, particular temperature conditions have to be maintained. Under these boundary conditions, the glyoxal accumulates in the form of high-boiling hydrates together with the acrylic acid in the column bottom.

The acrylic acid can subsequently be removed by distillation from the glyoxal hydrates in the aforementioned bottom liquid, in which case the glyoxal hydrates quite obviously no longer have, or at worst have only to a significantly reduced degree, the quality of monomeric glyoxal of promoting the undesired free-radical polymerization of acrylic acid.

In-house studies by the applicant have shown that the ability of glyoxal, as an impurity in acrylic acid, to promote the tendency of acrylic acid to undesired free-radical polymerization, is significantly more pronounced compared to other possible by-product aldehydes of a heterogeneously catalyzed partial gas phase oxidation of $C_3$ precursor compounds, for example acetaldehyde, formaldehyde, propionaldehyde, benzaldehyde, butyraldehyde, acrolein, based on equal molar impurity contents. The reason for this is presumably that, as has been found according to the CCSD (T) method (Coupled Cluster including Single, Double (and Triple) excitations) as a result of quantum-mechanical calculations of dissociation energies, the thermal requirement for splitting of monomeric glyoxal into two formyl radicals is firstly particularly low, and the resulting formyl radicals are secondly much more reactive than, for example, a hydrogen radical or a methyl radical.

Experiments in connection with literature studies, such as for example L'actualité chimique, May 1982, pages 23 to 31, and the literature cited within this article, have confirmed that hydrates of glyoxal no longer have the aforementioned pronounced polymerization-promoting action of monomeric or molecular glyoxal.

The glyoxal hydrates form two groups of hydrate types. The first group consists of the monomeric glyoxal monohydrate and of the monomeric glyoxal dihydrate:

Both of the above glyoxal hydrates form even under comparatively mild conditions. Relatively low temperatures, limited water contents are sufficient.

However, both the formation reactions of the monomeric glyoxal monohydrate and of the monomeric glyoxal dihydrate are markedly reversible reactions. In other words, neither of the two above hydrates any longer possesses the marked polymerization-promoting action of monomeric glyoxal, but monomeric glyoxal can reform from each of these hydrates, for example in the case of a moderate temperature increase, and are then capable in a manner known per se of promoting the undesired free-radical polymerization of acrylic acid.

Against the background of the above, formation of monomeric glyoxal monohydrate and/or monomeric glyoxal dihydrate in the rectification column in the azeotropic distillation may therefore be insufficient for a successful implementation of the teaching given in EP-A 1 396 484, even though these hydrates normally have an elevated boiling point and are normally enriched in the column bottom together with acrylic acid.

For a successful implementation of the process recommended in EP-A 1 396 484, according to in-house studies, the formation of the hydrates of "polyglyoxal" or "oligoglyoxal" is instead required. They form the second group of glyoxal hydrates. Diglyoxal hydrates and triglyoxal hydrates are shown by way of example below:

It is suspected that the formation of the polyglyoxal hydrates proceeds via the monomeric glyoxal dihydrate as an intermediate.

In contrast to the formation of the monomeric glyoxal hydrates, the formation of the polyglyoxal hydrates requires elevated temperatures and/or longer reaction times. They are generally formed to a significant degree only at temperatures above 50° C. Just like the monomeric glyoxal hydrates, the polyglyoxal hydrates also no longer have, or still have to a significantly lesser degree than monomeric glyoxal, at worst the polymerization-promoting tendency for acrylic acid which is typical of monomeric glyoxal. In contrast to the formation of the monomeric glyoxal hydrates, the polyglyoxal hydrates are, however, formed substantially irreversibly, at least under those conditions which are normally employed to remove acrylic acid from the product gas mixture of a heterogeneously catalyzed partial gas phase oxidation of a $C_3$ precursor compound of acrylic acid.

A successful application of the process recommended in EP-A 1 396 484 is thus comprehensible only on the basis of the formation of polyglyoxal hydrates. However, this requires, in a disadvantageous manner, both elevated temperatures and increased residence times.

US 2011/0036704 A1 describes a process for removal of crude acrylic acid from a product gas mixture, wherein glyoxal is formed as a by-product. For purification, the acrylic acid is absorbed in a high-boiling absorbent and the resulting absorbate is worked up by rectification. Absorbent from the liquid of the bottom space of the absorption column is distilled off and recycled. The glyoxal content of the crude acrylic acid is reduced by restricting the high-boiler residence time in the distillation unit for absorbent recycle.

US 2012/0085969 A1 discloses a process for inhibiting unwanted free radical polymerization of acrylic acid in a liquid phase P comprising glyoxal, in which at least one chemical compound of the element copper is added to the liquid phase P.

US 2010/0022734 A1 is related to a process for separating acrylic acid present as a main product and glyoxal present as a by-product in a product gas mixture, wherein the glyoxal is separated from acrylic acid by crystallization.

The processes known in the state of the art aiming at separating glyoxal from acrylic acid and inhibiting polymerization require considerable process changes, limitations or the addition of supplemental substances.

It is an object of the present invention to provide a process, which reduces undesired polymerization in the purification process of acrylic acid, typically occurring in the rectification column at a height, where crude acrylic acid is withdrawn. The glyoxal content in the mixture to be purified, comprising acrylic acid, should be depleted in an early stage of the purification process without addition of supplemental chemical components and without complex changes of the purification method or limitations to the synthesis step of acrylic acid.

This object is achieved by a process for production of acrylic acid comprising the following steps:
a) preparation of a product gas mixture by a catalytic gas-phase oxidation of at least one $C_3$ precursor compound to acrylic acid, wherein acrylic acid is formed as a main product of the catalytic gas-phase oxidation and glyoxal is formed as a by-product and the product gas mixture comprises acrylic acid and glyoxal,
b) cooling of the product gas mixture,
c) contacting the product gas mixture in countercurrent with an absorbent, wherein an absorbate A, comprising the absorbent and absorbed acrylic acid, is formed,
d) introducing a feed stream F comprising at least part of the absorbate A into a rectification column comprising a rectifying section and a stripping section,
e) enriching the absorbent in the stripping section and enriching acrylic acid in the rectifying section,
f) withdrawing a stream C of crude acrylic acid comprising at least 90% by weight of acrylic acid out of the rectifying section as a side stream,
wherein step c) is carried out in an absorption column comprising at least two cooling loops, a first cooling loop, wherein a high boiler fraction of the product gas mixture is condensed and a second cooling loop, wherein a low boiler fraction of the product gas mixture is condensed, wherein a portion of the absorbate A, which comprises the feed stream F, is removed from the absorption column at a side take-off, the side take-off being located at the first cooling loop or at a height of the absorption column between the first cooling loop and the second cooling loop, and wherein a temperature Tc of the absorbate A in the second cooling loop is at least 56° C.

In a preferred embodiment, the temperature Tc of the absorbate A in the second cooling loop is at least 58° C., more preferably 60° C. and most preferably in a range from 60° C. to 63° C.

The composition of the absorbate A varies over the height of the absorption column. By maintaining the temperatures in the second cooling loop to at least 56° C., a major part of the glyoxal present in the product gas mixture is separated off already in the absorption column, preferably leaving the absorption column at its upper part in form of acid water.

It is characteristic of this process that the acrylic acid is removed from the absorbate comprising it in dissolved form essentially in the rectifying section of a rectification column in the form of a crude acrylic acid whose proportion by weight of acrylic acid is at least 90% by weight. Frequently, the proportion by weight of such crude acrylic acid is even at least 95% by weight or at least 98% by weight. In general, the proportion by weight of aforementioned crude acrylic acid will, however, be not more than 99.9% by weight, in many cases not more than 99.8% by weight and often even not more than 99.7% by weight.

One reason for the advantage of the process according to the invention is that it does not require any quantitative restriction in the glyoxal by-product formation, and another is that it does not require the formation of polyglyoxal hydrates.

For the aforementioned reasons, the term glyoxal, as always in this document, unless stated otherwise, shall encompass not only monomeric glyoxal but also glyoxal chemically bound reversibly in the form of acetals and/or hemiacetals of glyoxal, more particularly, the term glyoxal in this document always also encompasses monomeric glyoxal monohydrate and monomeric glyoxal dihydrate.

An advantage of the inventive process is that, essentially without additional complexity, it also allows acrylic acid removals from the product gas mixtures which are relevant in accordance with the invention from a heterogeneously catalyzed partial gas phase oxidation of at least one $C_3$ precursor compound to acrylic acid to be managed in a satisfactory manner, in which the product gas mixture, based on the molar amount of acrylic acid present therein, comprises preferably at least 50 molar ppm of glyoxal, more preferably at least 150 molar ppm of glyoxal. Normally, the aforementioned glyoxal contents of the product gas mixture (on the same basis) will be not more than 1 mol %, preferably not more than 1000 molar ppm.

In other words, to determine the aforementioned glyoxal contents, based on the molar amount of acrylic acid present, in the product gas mixture, cooling the latter will convert at least the acrylic acid present therein, the hemiacetals and/or acetals of glyoxal present therein and the monomeric glyoxal present therein to the condensed phase, which will subsequently be analyzed as soon as possible after the generation thereof, for its content of glyoxal and of acrylic acid. The acrylic acid content can be determined in a manner known per se by chromatography, for example gas chromatography or by means of HPLC (high pressure liquid chromatography).

One advantage of the process according to the invention is thus that it is not reliant on the use of high-purity $C_3$ precursor compounds of acrylic acid for the heterogeneously catalyzed partial gas phase oxidation to prepare acrylic acid.

For example, for the heterogeneously catalyzed partial gas phase oxidation to prepare acrylic acid, it is possible to use a starting reaction gas mixture which, based on the molar amount of the at least one $C_3$ precursor compound present therein, contains a molar total amount of $C_2$ compounds, for example ethane, ethylene, acetylene, acetaldehyde, acetic acid and/or ethanol of at least 10 molar ppm, preferably at least 50 molar ppm.

The starting reaction gas mixture is that gas mixture which is supplied to the catalyst bed for the purpose of partial oxidation of the $C_3$ precursor compound present therein to acrylic acid. As well as the $C_3$ precursor compound, undesired impurities and molecular oxygen as the oxidizing agent, the starting reaction gas mixture generally also comprises inert diluent gases, for example $N_2$, $CO_2$, $H_2O$, noble gas, molecular hydrogen, etc. Any inert diluent gas is normally such that it remains unchanged to an extent of at least 95 mol %, or preferably to an extent of at least 98 mol %, of its starting amount in the course of the heterogeneously catalyzed partial oxidation.

The proportion of the $C_3$ precursor compound in the starting reaction gas mixture may, for example, be in the range from 4 to 20% by volume, preferably from 5 to 15% by volume and most preferably from 6 to 12% by volume.

Preferably, the at least one $C_3$ precursor compound is propylene, glycerol and/or acrolein.

Normally, the starting reaction gas mixture comprises, based on the stoichiometry of the partial oxidation reaction of the $C_3$ precursor compound to acrylic acid, an excess of molecular oxygen, in order to reoxidize the generally oxidic catalysts again.

In the case of subsequent application of the inventive process, this excess can be selected at a particularly high level, since an increasing oxygen excess is generally also accompanied by an increase in undesired secondary component formation of glyoxal.

In the context of the inventive process, it is similarly also possible to proceed in a more generous manner in the selection of the loading in l(STP)/h·l of the catalyst bed with the $C_3$ precursor compound. Greater loadings do not present any difficulties. In addition, it has been found that the by-production of glyoxal is promoted by elevated water vapor contents in the reaction gas mixture. The process according to the invention therefore is of relevance not least when the starting reaction gas mixture used for the heterogeneously catalyzed partial gas phase oxidation of the $C_3$ precursor compound comprises preferably at least 1% by weight of water, more preferably at least 3% by weight of water vapor. In general, the water vapor content of the starting reaction gas mixture will, however, not be more than 40% by weight, frequently not more than 30% by weight. It will be appreciated that aforementioned water vapor contents also promote the formation of glyoxal hydrates.

Otherwise, the process for heterogeneously catalyzed partial gas phase oxidation for preparing acrylic acid can be carried out in a manner known per se as described in the prior art.

When the $C_3$ precursor compound is, for example, propylene and/or acrolein, the heterogeneously catalyzed partial gas phase oxidation can be carried out, for example, as described in documents WO 2005/042459, WO 2005/047224 and WO 2005/047226.

When the $C_3$ precursor compound is, for example, propane, the heterogeneously catalyzed partial gas phase oxidation for preparing acrylic acid can be carried out, for example, as described in documents EP-A 608 838, DE-A 198 35 247, DE-A 102 45 585 and DE-A 102 46 119.

When the $C_3$ precursor compound is, for example, glycerol, the heterogeneously catalyzed partial gas phase oxidation for preparing acrylic acid can be carried out, for example, as described in documents WO 2007/090991, WO 2006/114506, WO 2005/073160, WO 2006/114506, WO 2006/092272 or WO 2005/073160.

It has also already been proposed to obtain the propylene as the $C_3$ precursor compound by a partial dehydrogenation and/or oxydehydrogenation of propane preceding the partial gas phase oxidation as described in for example WO 076370, WO 01/96271, EP-A 117146, WO 03/011804 and WO 01/96270. This route can likewise be taken in the context of the inventive process.

Generally, a great variety of absorbents can be used in the absorption column including aqueous and organic solvents. Preferably, the absorbent is a high-boiling adsorbent. High-boiling absorbents are understood to mean absorbents whose boiling point at standard pressure is above that of acrylic acid. Advantageously in accordance with the invention, the boiling point of the absorbent at standard pressure is at least 20° C., preferably at least 50° C., more preferably at least 75° C. and most preferably at least 100° C. or at least 125° C. above the boiling point of acrylic acid, which is 141° C. at 1 atm, at the same pressure. In general, the boiling point of the absorbent used for the process according to the invention at standard pressure is at values of at least 400° C., frequently at least 350° C. and in many cases also at least 300° C. or at least 280° C.

In a manner particularly suitable for the process according to the invention, the boiling point of the absorbent used for the process according to the invention, at standard pressure, is at values in the range from 200° C. to 350° C., preferably in the range from 200° C. to 300° C. For example, useful absorbents include all of those which satisfy the aforementioned boundary conditions and are recommended in the documents DE-A 103 36 386, DE-A 024 49 780, DE-A 196 27 850, DE-A 198 10 962, DE-A 043 08 087, EP-A 0 722 926 and DE-A 044 36 243.

In general, the high-boiling absorbents are organic liquids.

For the process according to the invention, particular preference is also given to absorbents which consist to an extent of at least 70% by weight of those organic molecules which do not comprise any externally active polar groups and are therefore, for example, incapable of forming hydrogen bonds.

Absorbents which are particularly favorable in accordance with the invention are, for example, diphenyl ether, diphenyl, corresponding to biphenyl, mixtures, known as Diphyl® and consisting of 70% to 75% by weight of diphenyl ether and 25% to 30% by weight of diphenyl, and also dimethyl phthalate, diethyl phthalate and mixtures of a first constituent, the first constituent consisting of 70% to 75% by weight of diphenyl ether and 25% to 30% by weight diphenyl, and dimethyl phthalate or the first constituent, the first constituent consisting of 70% to 75% by weight of diphenyl ether and 25% to 30% by weight diphenyl, and diethyl phthalate or the first constituent, the first constituent consisting of 70% to 75% by weight of diphenyl ether and 25% to 30% by weight diphenyl, dimethyl phthalate and diethyl phthalate. A group of mixtures which is very particularly suitable as absorbents for use in accordance with the invention is that of those composed of 75% to 99.9% by weight of the first constituent, the first constituent consisting of 70% to 75% by weight of diphenyl ether and 25% to 30% by weight diphenyl and 0.1% to 25% by weight of dimethyl phthalate and/or diethyl phthalate. Suitable diethyl phthalate for this purpose is, for example, at least 99% by weight diethyl phthalate from BASF SE.

Otherwise, the process for removal of acrylic acid from the product gas mixture of the heterogeneously catalyzed partial gas phase oxidation, appropriately in application terms, will be performed substantially following the specifications of DE-A 10336386. It is also possible to proceed as described in the flow diagrams of DE-A 19606877 and DE-A 1960687. Alternatively, it is possible to proceed as in DE-A 10251138.

Further, the process according to the invention should be performed such that the bottom liquid present in the bottom space of the absorption column has a minimum proportion by weight of heavy metals/heavy metal ions, especially transition metal ions, or of any metals/metal ions at all, since they can enhance the undesired polymerization tendency of acrylic acid. Preferably, this proportion by weight is less than 1 ppm by weight per metal or per heavy metal or per transition metal, based on the weight of the bottom liquid. These metals include especially the metals Cr, Co, Cd, Fe, Mn, Mo, Ni, Sn, V, Zn, Zr, Ti, Sb, Bi and Pb, but also Al, Ca, Mg, K and Li.

Possible sources for a metal contamination as described above include especially the catalyst bed used for the heterogeneously catalyzed partial gas phase oxidation and the manufacturing materials used for the equipment involved. This is in particular because the catalysts used as active materials for the partial oxidation are normally multimetal oxide materials comprising Mo, Bi and Fe and/or multimetal oxide materials comprising Mo and V. Owing to its water vapor content, the reaction mixture is capable, for example, of promoting the discharge of molybdenum oxides from the active materials. Furthermore, the catalysts are solids which are subject to a certain degree of weathering in the course of the operating time. As a consequence, there may be a discharge of fine catalyst dust with the reaction gas mixture. Appropriately, the process for heterogeneously catalyzed partial gas phase oxidation will therefore be performed as detailed in WO 2005/042459 or in WO 2005/113127 using the example of a two-stage heterogeneously catalyzed partial gas phase oxidation of propene to acrylic acid.

The materials used for the equipment involved are especially those recommended in DE-A 10336386. The material used is preferably 1.4571 according to DIN EN 10020:2000-07, advantageously with a very smooth surface. It will be appreciated that it is also possible to use the materials recommended in WO 2005/007609. Optionally, substances which complex metals, for example EDTA, can be added to the bottom liquid in the bottom space of the absorption column.

Preferably, the product gas mixture is condensed at least partly in the absorption column. The adsorption column preferably has baffles which effect separation, in particular having packings and/or trays, preferably bubble trays, sieve trays, valve trays and/or dual-flow trays. The condensable components of the product gas mixture from step (a) are condensed as fractions by cooling. Since, owing to the impurities and diluent gases, the gas mixture contains a high boiler, medium boiler and low boiler fraction and uncondensable components, one or more side take-offs can be provided at the appropriate points in the column. In contrast to a conventional condensation, a condensation in a column thus permits separation into the individual components. Suitable columns comprise at least one cooling apparatus, for which all conventional heat transfer apparatuses or heat exchangers in which the heat formed in the condensation is removed indirectly or externally are suitable. Tube-bundle heat exchangers, plate-type heat exchangers and air coolers are preferred. Suitable cooling media are air in the corresponding air coolers and cooling liquids, in particular water, in other cooling apparatuses.

Since the acrylic acid-containing gas mixture contains a plurality of fractions, it is expedient to install a plurality of cooling apparatuses in various sections of the column, for example a cooling apparatus in the lower section of the column for condensing the high boiler fraction and a cooling apparatus at the top of the column for condensing the low boiler fraction. The fraction containing the acrylic acid is removed in the middle part of the column, via one or more side take-offs.

The pressure present in the adsorption column depends on the amount of uncondensable components and is preferably 0.5 to 5, in particular 0.8 to 3, bar absolute pressure. The exact operating conditions for the column, such like pressure, connection and arrangement of the cooling apparatus (es), arrangement of the side take-off/side take-offs for removing acrylic acid, choice of the column height and of the column diameter, number and spacing of the baffles/trays effecting separation in the column or type of column baffles effecting separation, can be determined by a person skilled in the art in experiments customary in the field, depending on the separation task.

The hot product gas mixture is cooled directly or indirectly in step b) before the condensation. Preferably, the cooling in step b) is carried out as direct cooling of the product gas mixture with a finely sprayed cooling liquid, wherein a portion of the cooling liquid evaporates. This direct cooling can also be described as quenching.

In the case of direct cooling, it is preferable to cool the gas mixture with the aid of the high boiler fraction condensed from the gas mixture. The absorption column preferably comprises a bottom space, from which a first portion of the bottom liquid, comprising the absorbent is withdrawn and applied in the direct cooling as the cooling liquid. Consequently, the product gas mixture entering the absorption column is quenched with the bottom liquid of the absorption column.

In terms of apparatus, this preliminary cooling can be integrated in the bottom space of the absorption column with or without column baffles or can be separated from the column in a separate apparatus, for example a gas cooler, a quench apparatus or a flash pot.

The absorption column is preferably constructed in a way that the second cooling loop is in a second position counting all cooling loops in the absorption column from the bottom space of the absorption column upwards. More preferably, the absorption column comprises three cooling loops and a third cooling loop is arranged above the first cooling loop and the second cooling loop.

Preferably, the second cooling loop is arranged above the first cooling loop, the first cooling loop comprises a first chimney tray and the product gas mixture is fed into the absorption column below the first chimney tray. The chimney tray can also be described as collecting trail. The second cooling loop preferably comprises a second chimney tray.

The chimney tray functions simultaneously as collecting tray for a liquid which accumulates thereon, for example accumulating absorbate. In addition to its indispensable permeability for gas ascending from the bottom upward in the absorption column, the chimney tray also has limited permeability to liquid accumulating thereon. It is also possible in principle for the aforementioned chimney trays to be completely impervious to liquid which accumulates thereon.

As separating internals between the chimney trays, tray types known by the person skilled in the art are applicable such as tunnel trays, fixed valve trays, sieving trays or bubble cap trays or packings.

In a particularly preferred embodiment, the condensation of the reaction gas mixture takes place in absorption column as follows, it being possible to organize the absorption column in various sections in which the following different process functions are performed:

1. Bottom Space: Cooling of the Hot Product Gas Mixture

The hot product gas mixture is passed into the bottom space and cooled. This can be effected by indirect cooling, for example by means of a heat exchanger, or by direct cooling with, as the cooling medium, high boiler fraction condensed in the next section of the column.

2. First Cooling Loop: Condensation of the High Boiler Fraction

In the region of the first cooling loop, the heat of condensation is removed externally via the first cooling loop by means of a heat exchanger with, for example, water as cooling medium, by removing condensed high boiler fraction from the column, cooling said fraction by means of the heat exchanger and recycling a part of the cooled, condensed, high boiler fraction to the column while the other part, usually less than 1% by weight, based on 100% by weight of condensate, in a side take-off, is removed. The recycled, condensed high boiler fraction is fed countercurrent to the ascending gas.

3. First Cooling Loop to Side Take-Off: High Boiler Concentration

Between the first cooling loop and the side take-off, distillative concentration and condensation of the high boiler fraction from the gas stream fed countercurrent upward are effected toward the first cooling loop.

4. Side Take-Off Removal of the Acrylic Acid Rich Stream Comprising the Feed Stream F Acrylic acid is removed via the side take-off.

5. Side Take-Off to Second Cooling Loop: Concentration of the Medium Boiler Fraction In the region between the side take-off and the second cooling loop, the medium boiler fraction from the gas stream fed countercurrent upward is concentrated, the medium boiler fraction being concentrated toward the side take-off.

6. Second Cooling Loop: Condensation of the Low Boiler Fraction

In the region of the second cooling loop, the low boiler fraction from the gas stream fed countercurrent upward is condensed. The heat of condensation is removed externally via the second cooling loop by means of a heat exchanger with, for example, water as cooling medium, by removing condensed low boiler fraction and cooling it and recycling a part of the cooled, condensed low boiler fraction to the column while the other part is removed. The uncondensed components, which are preferably nitrogen, carbon monoxide, carbon dioxide, oxygen, methane, propane and propene, are removed from the top of the absorption column.

Preferably, the second cooling loop comprises an indirect heat exchanger, more preferably an air cooler. The air cooler can comprise fine tubes in which the withdrawn mixture to be cooled is conducted from the top downward and which are supplied from outside with ambient air with the aid of ventilators.

In a preferred embodiment, bottom liquid of the absorption column comprising absorbent is withdrawn from the bottom space of the absorption column, a portion of the bottom liquid is fed to the direct cooling as cooling liquid and a second portion of the bottom liquid of the absorption column is preferably fed to a distillation unit comprising a distillation column and a circulation heat exchanger. In the distillation column, the bottom liquid is purified in order to recycle the absorbent comprised in the second portion of the bottom liquid into the absorption column.

The supply of the bottom liquid withdrawn from the bottom space of the absorption column to the distillation unit is for the purpose of recovering absorbent present in the bottom liquid, before undesired high-boiling by-products, which also comprise high-boiling secondary constituents are discharged from the process for removal of acrylic acid as described in for example DE-A 24 49 780. These by-products to be discharged from the removal process include, for example, also polymers of acrylic acid which form in an unavoidable manner only in the course of the performance of the removal process, and resinified cracking products of the absorbent, but also polymerization inhibitors and any catalyst dust present in the product gas mixture of the partial oxidation. The boiling point of these high-boiling secondary constituents is, both at standard pressure and under the conditions of the distillation, typically above that of the absorbent.

Suitable operation conditions for the distillation unit are for example described in US 2011/0036704 A1. Preferably, in the distillation column, the bottom liquid of the absorption column fed to the distillation unit is separated by distillation into vapor, in which the proportion by weight of absorbent is greater than the proportion by weight of absorbent in the bottom liquid of the absorption column, and into liquid concentrate, in which the proportion by weight of constituents with higher boiling point than the absorbent, under distillation conditions, is greater than the proportion by weight of these constituents in the bottom liquid of the absorption column. More preferably, a stream of the vapors, optionally after cooling and/or condensation thereof in an indirect heat exchanger, is recycled into the absorption column above the first chimney tray, most preferably above the second chimney tray.

The circulation heat exchanger of the distillation unit is understood to mean an indirect heat exchanger present outside the distillation column. Indirect heat exchangers have at least one primary space and at least one secondary space. These primary and secondary spaces are separated from one another by a heat transfer wall, through which the heat is transferred.

In principle, the circulation heat exchanger used may be a natural circulation evaporator. Advantageously, however, a forced circulation evaporator or forced circulation heat exchanger is used according to for example FIG. 2 of WO 2005/007609.

The inventive process preferably further comprises a stripping unit, wherein low boilers are stripped out of the absorbate A in the stripping unit between step c) and step d).

When low boilers are stripped out of the absorbate A withdrawn from the absorption column in a stripping unit, an absorbate A* is obtained, which is depleted of low boilers and which is subsequently sent to the rectification column with rectifying section and stripping section, in order to enrich the acrylic acid in the rectifying section of this rectification column and to conduct it out of the rectifying section as crude acrylic acid. A reduction in the glyoxal content of the crude acrylic acid can additionally or also be brought about by performing the stripping particularly intensively. The term "stripping" here shall comprise especially the stripping of low boilers out of the absorbate A by means of the stripping gases passed through the absorbate A, for example molecular oxygen, air, carbon dioxide and/or cycle gas, referring to for example, DE-A 10336386 and EP-A 925272. However, it shall also include desorption, corresponding to the removal of an absorbed low boiler from the absorbate, by, for example, heating or by reducing the pressure in the gas phase. It will be appreciated that it also comprises all possible combinations of the individually encompassed process measures. The intensity of the stripping is promoted by increasing the stripping temperature, reducing the stripping pressure and by increasing the flow of the stripping gas stream used based on a stream of absorbate A.

Preferably, the stripping of the absorbate A will be performed in a stripping column in which the stripping gas and the absorbate A are conducted in countercurrent to one another. For example, the stripping can be performed in analogy to the remarks in DE-A 4308087 and in DE-C 2136396. In principle, however, it is also possible to strip as in EP-A 1041062. When the stripping is performed in the form of stripping out with a stripping gas, a suitable stripping column is especially a tray column. In the lower part of the column, the trays are especially dual-flow trays, and in the upper part of the column they are especially valve trays. The absorbate A is introduced in the top region of the stripping column, and the stripping gas is, appropriately in application terms, conducted into the stripping column below the lowermost dual-flow tray and above the liquid level.

Preferably, part of the absorbent, which is withdrawn from the stripping section of the rectification column is recycled into the absorption column. The part of the absorbent, which is withdrawn from the stripping section of the rectification column and recycled into the absorption column, preferably comprises a proportion by weight of acrylic acid of not more than 1% by weight.

An acrylic acid-depleted gas stream which flows out of the absorption column is generally also subjected to a condensation of the water vapor normally present therein. The resulting condensate is referred to as acid water. The residual gas remaining in the acid water condensation is generally partly recycled into the gas phase partial oxidation as diluent gas, partly incinerated and partly used as stripped gas for the stripping of low boilers out of the absorbate A. Prior to the aforementioned further use as stripping gas, it is preferably scrubbed with absorbent conducted out of the stripping section of the rectification column, before the latter is recycled into the absorption column. Prior to this recycling, it is appropriate to extract a portion with acid water. The acid water extract obtained is advantageously stripped with residual gas to be supplied to the incineration thereof. The stripping gas which flows out of the low boiler stripping column and is laden with low boilers is appropriately conducted into the direct cooler.

BRIEF DESCRIPTION OF THE DRAWINGS

The present invention is described in more detail at hand of the accompanying drawings, in which.

Figure 1:
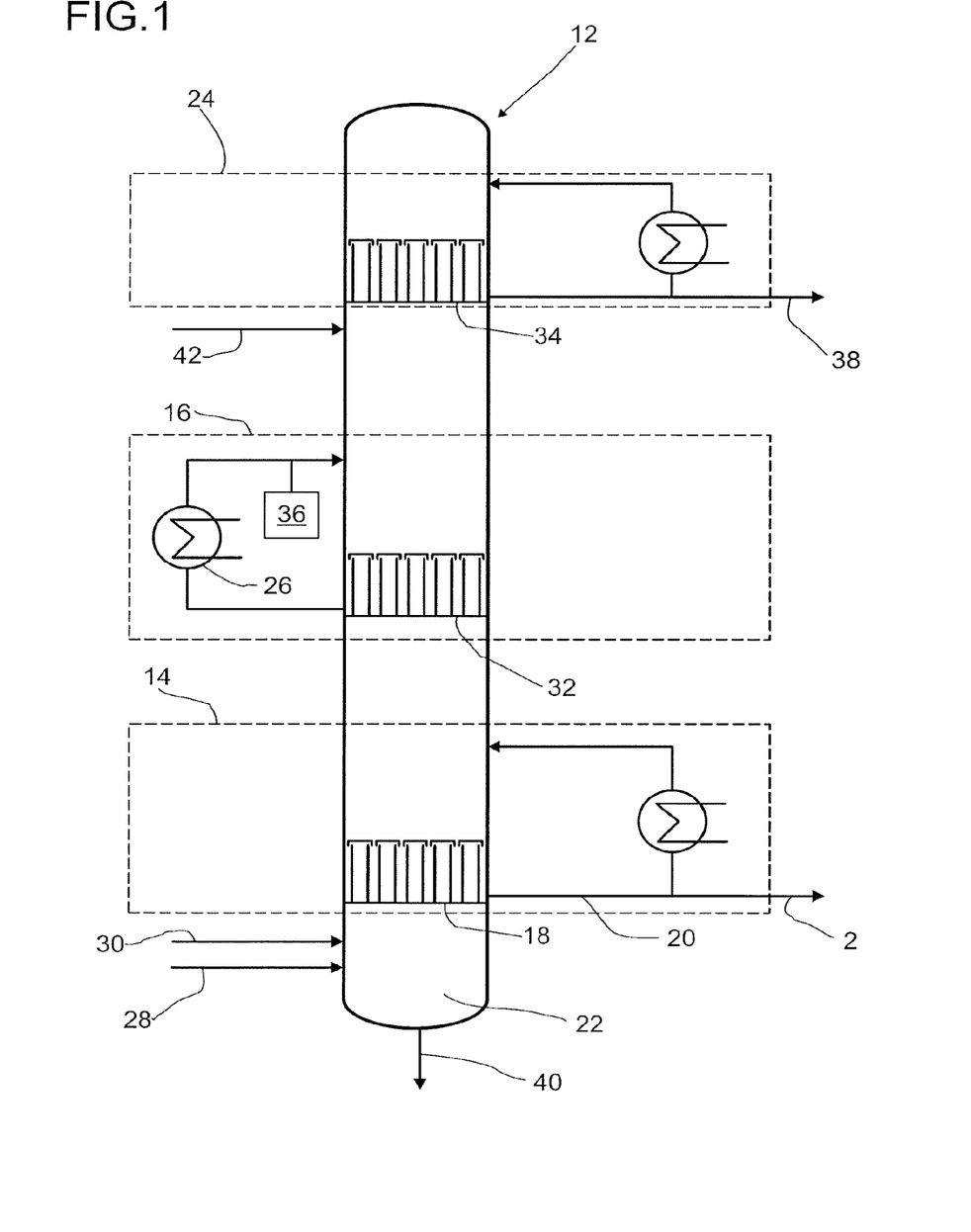
FIG. 1 shows an absorption column applicable in the inventive process.

FIG. 1 shows an absorption column 12, applicable in the inventive process. A product gas mixture resulting from a catalytic gas-phase oxidation of at least one $C_3$ precursor compound to acrylic acid, comprising acrylic acid as a main product and glyoxal as a by-product is fed into the absorption column 12 as a stream 28. The product gas mixture is directly cooled in a bottom space 22 of the absorption column 12 by quenching with a cooling liquid. The cooling liquid enters the absorption column 12 as a stream 30.

The precooled product gas mixture ascends in the absorption column 12 and is contacted with an absorbent in a countercurrent mode. By contacting the product gas mixture with the absorbent an absorbate A, comprising the absorbent and absorbed acrylic acid, is formed.

The absorption column 12, comprises three cooling loops 14, 16, 24. A second cooling loop 16 is arranged above a first cooling loop 14 and a third cooling loop 24 is arranged above the second cooling loop 16. Each cooling loop 14, 16, 24 comprises a chimney tray 18, 32, 34. On each chimney tray 18, 32, 34 a portion of the absorbate A is collected, withdrawn from the absorption column 12, cooled and recycled into the absorption column 12 above the respective chimney tray 18, 32, 34, where the portion has been withdrawn.

For cooling, the second cooling loop 16 comprises an air cooler 26. After the air cooler 26 and before the withdrawn portion of the absorbate A is recycled from the second cooling loop 16 into the absorption column 12, the temperature of the cooled portion of the absorbate A is measured by a temperature sensor 36. According to the invention, the temperature of the absorbate A in the second cooling loop 16 measured before its re-entrance into the absorption column 12 by the temperature sensor 36 is at least 56° C. By maintaining the temperatures in the second cooling loop of at least 56° C., a major part of the glyoxal present in the product gas mixture is separated off already in the absorption column 12 with a stream 38 of acid water.

From the bottom space 22, a bottom liquid comprising the absorbent is withdrawn as a stream 40. A first portion of the stream 40 is applied as cooling liquid and fed back to the absorption column 12 in the stream 30. A second portion of stream 40 is purified and recycled into the absorption column as a stream 42.

Figure 2:
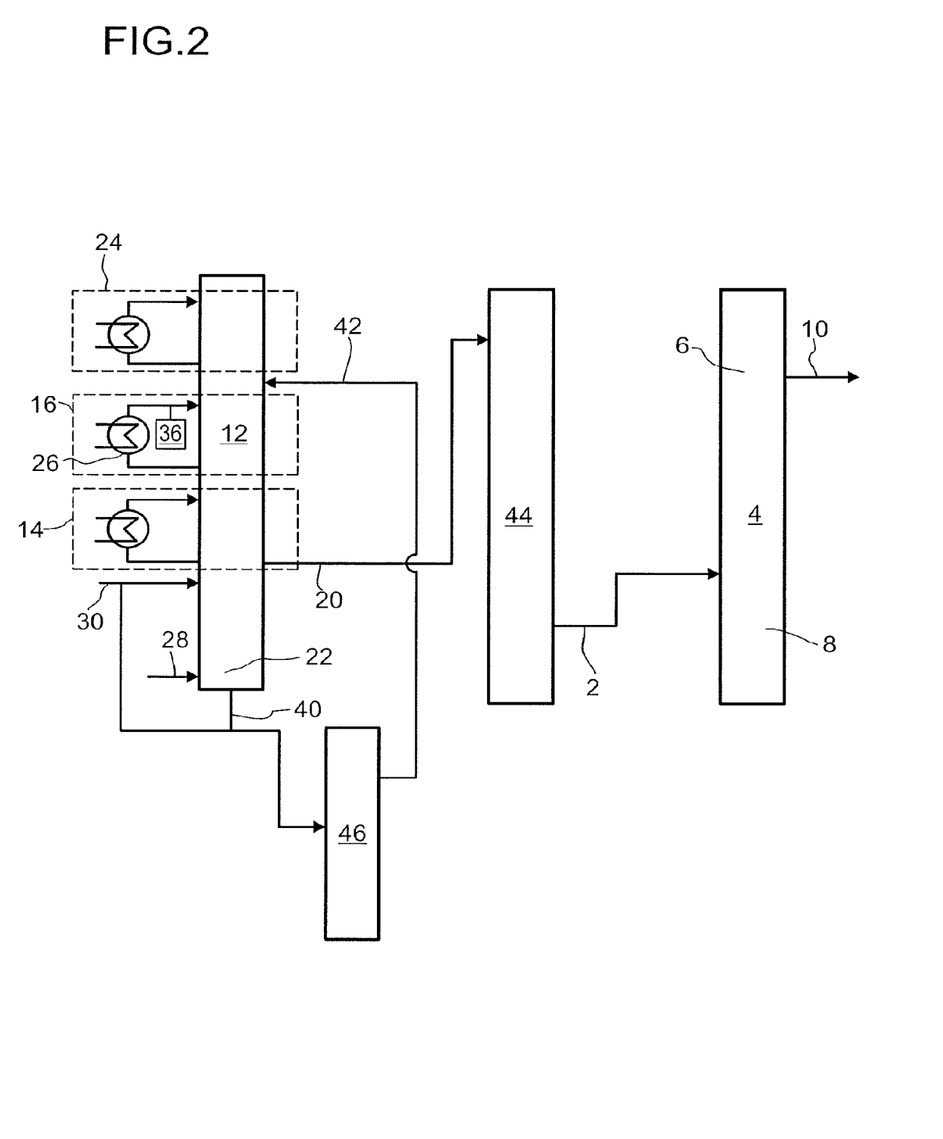
FIG. 2 shows a flow chart of a preferred embodiment of the inventive process.

FIG. 2 shows a preferred embodiment of the inventive process. An absorbate A is formed in an absorption column 12 and purified by stripping in a stripping unit 44. From the stripping unit 44 a feed stream F 2 is introduced into a rectification column 4, comprising a rectifying section 6 and a stripping section 8. Crude acrylic acid is withdrawn as a stream C 10 from the rectifying section 6.

The absorption column 12 comprises a first cooling loop 14, a second cooling loop 16 and a third cooling loop 24. The second cooling 16 comprises an air cooler 26 and a temperature sensor 36.

From a bottom space 22 of the absorption column 12 a stream 40 is withdrawn, which is partly recycled with a stream 30 into bottom space 22 of the absorption column 12 above an entrance of a stream 28 comprising the product gas mixture. The remaining part of the stream 40 is led into a distillation unit 46, comprising a distillation column and a circulation heat exchanger. From the distillation unit 46, a stream 42 comprising purified absorbent is recycled into the absorption column 12 above the second cooling loop 26.

EXAMPLE AND COMPARATIVE EXAMPLE

Two plants for acrylic acid production according to FIGS. 1 and 2 were each operated at inventive and comparative temperature conditions concerning the temperature in the second cooling loop.

To experimentally determine the molar amount of glyoxal present in a liquid phase P in such forms, the procedure should preferably be as follows.

First, a derivatization solution D is prepared. To this end, 2.0 g of a 50% by weight solution of 2,4-dinitrophenylhydrazine, available for example from Aldrich with a purity of at least 97%, are dissolved at a temperature of 25° C. in 62 ml of a 37.0% by weight aqueous hydrochloric acid, available for example from Aldrich with a purity of at least 99.999%. The resulting solution is subsequently, likewise at a temperature of 25° C., stirred into 335 g of distilled water. After stirring at 25° C. for 1 hour, the derivatization solution D is obtained by filtration as the resulting filtrate.

Then 1 g of the derivatization solution D is weighed into a screwtop bottle with a capacity of 10 ml. If required, the amount of 1 g can be increased in a corresponding manner. Subsequently, a sample of the liquid phase to be analyzed, the amount of which is in the range from 0.15 g to 2.0 g, is weighed into the screwtop bottle thus filled.

The entire contents of the screwtop bottle are then mixed by shaking and then left at a temperature of 25° C. for a period of 10 minutes. During this time, the corresponding hydrazone H of monomeric glyoxal forms from the monomeric glyoxal present in the screwtop bottle by chemical reaction with 2,4-dinitrophenylhydrazine. During this time, the 2,4-dinitrophenylhydrazine, however, also removes the monomeric glyoxal, in the form of the hydrazone H, bound reversibly in the hemiacetals and/or acetals of glyoxal which are present in the screwtop bottle and contain monomeric glyoxal bound reversibly therein (in contrast, there is essentially no corresponding removal of monomeric glyoxal from hemiacetals and/or acetals with essentially irreversible glyoxal formation).

Addition of 0.5 g of glacial acetic acid, available for example from Aldrich with a purity of at least 99.8%, to the screwtop bottle subsequently freezes the hydrazone formation which has occurred. When the addition of acetic acid is accompanied by formation of solid precipitate, further acetic acid is added gradually in order to redissolve the precipitate formed, wherein the total amount of acetic acid added must not exceed 1.0 g. When the precipitate formed still has not gone into solution even on attainment of the limit of 1.0 g of the total amount of acetic acid addition allowed, 0.5 g of dimethyl phthalate is weighed in. If this too is incapable of dissolving the precipitate formed, the amount of dimethyl phthalate added is increased gradually in order to bring about this dissolution, wherein the total amount of dimethyl phthalate added must not exceed 1.0 g. If the precipitate formed still has not gone into solution even on attainment of the limit of 1.0 g of the total amount of dimethyl phthalate addition allowed, 2 g of a mixture G of 9 g of acetonitrile and 1 g of dimethyl phthalate are added. If this addition too is incapable of dissolving the precipitate, the amount of mixture G added is increased gradually in order to bring about this dissolution. Normally, the total amount of mixture G added in order to bring about the dissolution of the precipitate does not exceed 5 g. All above dissolution tests are carried out at 25° C.

The solution of the hydrazone H obtained in the screwtop bottle as described is subsequently analyzed for its hydrazone content by means of HPLC using the following operating conditions. The molar amount thereof results directly in the molar amount of glyoxal present in the sample of the liquid phase to be analyzed:

Chromatography column to be used: Waters Symmetry $C_{18}$, 150×4.6 mm, 5 µm, from Waters Associates, Milford, Mass., USA;

Injection volume of the solution to be analyzed: 50 µl at time t=0;

Temperature: 40° C.;

Eluent flow rate: 1.5 ml/min;

Analysis time: 17 min;

Equilibration time: 8 min;

Eluent:

in the period t from more than 0 min to 15 min, a mixture of 30% by weight of acetonitrile, 50% by weight of water and 20% by weight of tetrahydrofuran, each HPLC grade;

in the period from more than 15 min to 17 min, a mixture of 65% by weight of acetonitrile, 30% by weight of water and 5% by weight of tetrahydrofuran;

in the period from more than 17 min to 25 min, a mixture of 30% by weight of acetonitrile, 50% by weight of water and 20% by weight of tetrahydrofuran. Then the column is equilibrated and ready for use again for the next analysis.

The retention time of the glyoxal as the hydrazone H is 7.613 min under the above conditions. The analysis is effected by means of monochromatic radiation of wavelength 365 nm. The analysis method employed is absorption spectroscopy.

The variation of the eluent over the elution time ensures an increased separating action (in general, the liquid phase to be analyzed, as well as glyoxal, also comprises other by-product aldehydes and/or by-product ketones which form the particular corresponding hydrazone with 2,4-dinitrophenyl-hydrazine).

To calibrate the HPLC method, appropriately in application terms, a solution of monomeric glyoxal in methanol will be used, which comprises 50 ppm by weight of monomeric glyoxal. For this purpose, it is treated by means of the derivatization solution D as described above and then subjected to the HPLC analysis described.

In the plants, the absorption column comprised 13 fixed valve trays between the first and the second chimney tray and 21 fixed valve trays between the second and the third chimney tray. Above the third chimney tray 11 fixed valve trays were present.

Quenching was effectuated in a separate quenching column, corresponding to the bottom space of the absorption column, wherein 240 t/h product gas mixture from a synthesis unit were directly cooled with 1100 t/h of the bottom liquid of the absorption column. Further, from the bottom space of the absorption column 62 kg/h of the bottom liquid, which was enriched in high boiling impurities, were withdrawn from the absorption column and removed from the process. 245 t/h cycle gas were withdrawn from the upper part of the absorption column.

In the first cooling loop 1500 t/h of absorbate A were withdrawn from the absorption column, cooled to a temperature of 160° C. and recycled back into the absorption column. At a side take-off at the first cooling loop, 230 t/h of absorbate A were withdrawn from the absorption column and conducted towards the rectification column. Further, 32 t/h of absorbate A were led through the first chimney tray towards the bottom space of the absorption column.

On the first chimney tray a volume of approximately 30 m³ of the absorbate A were collected, having a temperature of 115° C. and the following composition:

TABLE 1

| Content in % by weight | Constituent |
| --- | --- |
| 30 | acrylic acid |
| 54 | Diphyl ®, comprising 75 wt.-% diphenyl ether and 25 wt.-% diphenyl |
| 12.20 | dimethyl phthalate |
| 0.21 | benzaldehyde |
| 0.37 | maleic anhydride |
| 0.27 | acetic acid |
| 0.177 | water |
| 0.5507 | benzoic acid |
| 0.28 | phthalic acid |
| 1.38 | diacrylic acid |

In the second cooling loop, 2000 t/h of the absorbate A were withdrawn from the absorption column, cooled and recycled into the absorption column. 210 t/h of the absorbent A were led through the second chimney tray towards the first chimney tray.

On the second chimney tray a volume of approximately 30 m³ of the absorbate A were collected, having a temperature of 77.7° C. and the following composition:

TABLE 2

| Content in % by weight | Constituent |
| --- | --- |
| 20.40 | acrylic acid |
| 5.50 | acetic acid |
| 3.47 | water |
| 53.15 | Diphyl ® comprising 75 wt.-% diphenyl ether and 25 wt.-% diphenyl |
| 12.30 | dimethyl phthalate |
| 0.198 | benzaldehyde |
| 2.20 | formic acid |
| 0.295 | maleic anhydride |
| 0.5345 | benzoic acid |
| 1.47 | diacrylic acid |

From the third cooling loop 374 t/h of the absorbate A were recycled into the absorption column with a temperature of 25° C. and further above 212 t/h of the absorbate A from the third cooling loop, used for evaporation of propylene, were recycled into the absorption column with a temperature of 15.9° C. From the third chimney tray, 12 t/h of acid water with a temperature of 40° C. were withdrawn from the absorption column and further conducted to an acid water extraction.

On the third chimney tray a mass of approximately 30 tons of the absorbate A were collected, having a temperature of 40° C. and the following composition:

TABLE 3

| Content in % by weight | Constituent |
| --- | --- |
| 9.40 | acrylic acid |
| 5.07 | acetic acid |
| 65.60 | water |
| 12.40 | Diphyl ® comprising 75 wt.-% diphenyl ether and 25 wt.-% diphenyl |
| 2.10 | dimethyl phthalate |
| 3.42 | formaldehyde |
| 0.70 | formic acid |

Figure 3:
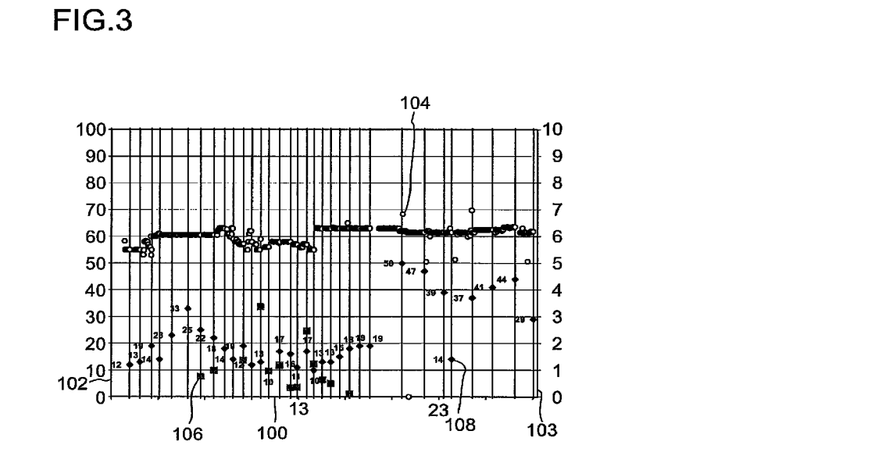
FIGS. 3 and 4 show the runtime between two shutdowns and the temperature in the second cooling loop in two different plants and FIG. 5 shows the dependency of the glyoxal concentration on the temperature.
Figure 4:
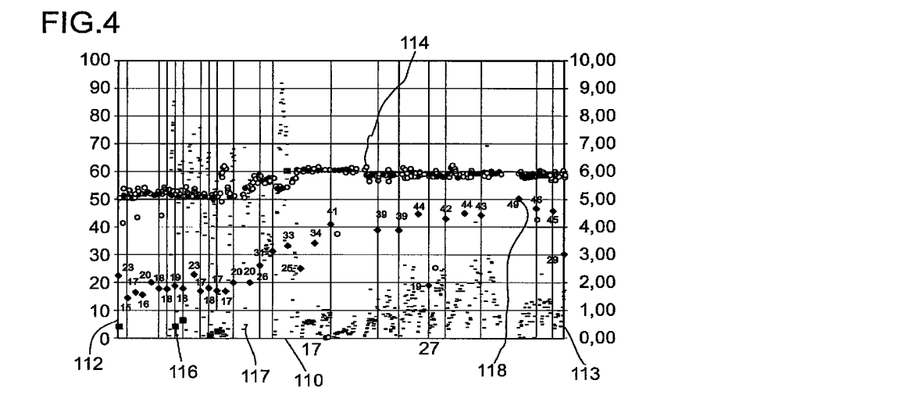

FIGS. 3 and 4 show the results from the examples and comparative examples. FIG. 3 is assigned to a first plant and FIG. 4 is assigned to a second plant. The runtime in days between two shutdowns and amount of polymer, which had to be removed during the shutdown, as well as the glyoxal concentration in the crude acrylic acid is represented in dependency of the temperature in the second cooling loop.

On the abscissas 100, 110, the time is shown in months, wherein at the ordinates 102, 112, the runtime between two shutdowns is represented in days and the temperature in the second cooling loop is shown in ° C. The abscissa 112 in FIG. 4 additionally represents the glyoxal concentration in the crude acrylic acid in weight ppm. On the secondary ordinates 103, 113, the amount of polymer, which had to be removed at each shutdown, is given in tons.

Each effectuated shutdown is marked in the diagrams of FIGS. 3 and 4 by a vertical line. The shutdowns were effectuated at the latest possible point of time, when too much polymer was accumulated in the rectification column and the pressure difference in the rectification column therefore increased. A larger distance between two vertical lines indicates that longer runtimes between two shutdowns were possible.

Circles 104, 114 represent the temperature of the absorbate A in the second cooling loop before re-entering the absorption column. Grey squares 106, 116 stand for the amount of polymer in tons, which had to be removed at the corresponding shutdown. Diamonds 108, 118 indicate the number of days of the runtime between two shutdowns. In FIG. 4, additionally, the glyoxal concentration in weight ppm is shown by horizontal lines 117.

In the first plant, according to FIG. 3, the temperature in the second cooling loop was enhanced to a temperatures between 62° C. and 63.5° C. after approximately 14 months. Initially, applying the comparative lower temperatures in the second cooling loop, considerable amounts of more than 3 tons polymer were formed in the rectification column and had to be removed during the shutdowns. A shutdown was necessary regularly after 10 to 20 days for polymer removal.

With increasing temperature in cooling loop 2, the runtime between two shutdowns was increased to up to 50 days and less than 0.1 tons of polymer had to be removed during shutdowns.

In the second plant, according to FIG. 4, the temperature in the second cooling loop was increased from 52° C. to more than 57° C. At initial low temperature conditions a shutdown had to be effectuated approximately every 20 days. By the temperature increase, the glyoxal concentration in the crude acrylic acid was reduced from up to 90 weight ppm to a glyoxal concentration of less than 30 weight ppm resulting in runtimes of up to 50 days. After the temperature increase, less than 0.1 tons of polymer had to be removed from the rectification column.

Figure 5:
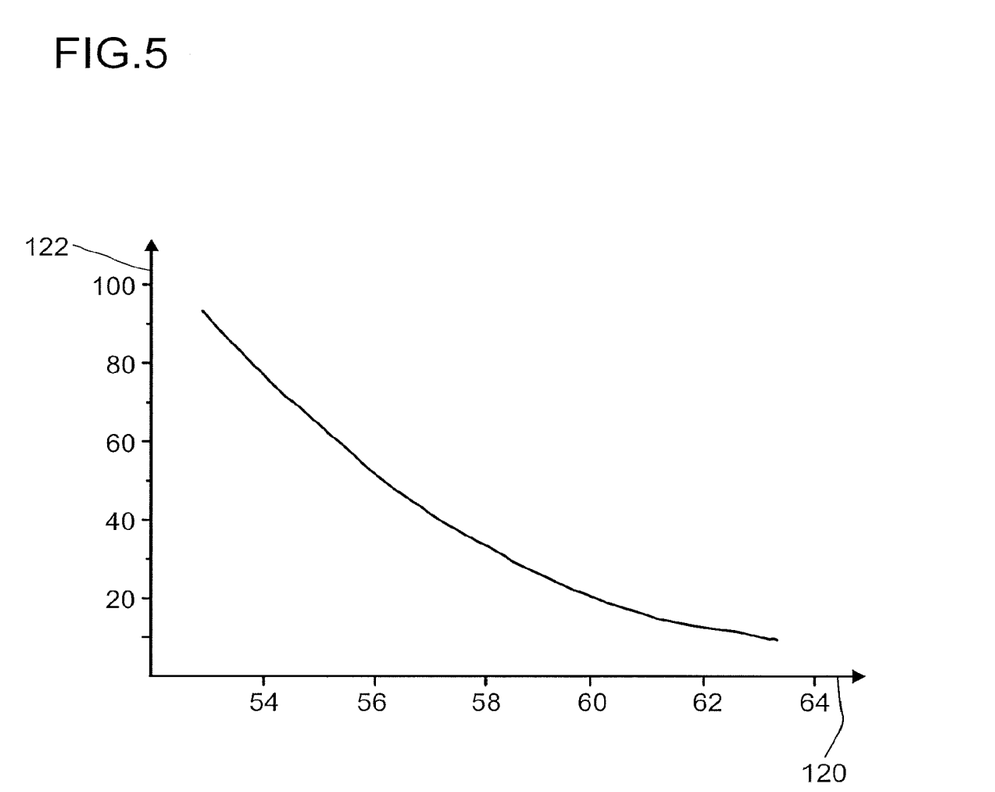

Based on the data from the first plant, FIG. 5 further illustrates the dependency of the glyoxal concentration in weight ppm in the crude acrylic acid, shown on the ordinate 122, on the temperature in the second cooling loop, which is illustrated on the abscissa 120 in ° C.

REFERENCE NUMERALS 2 feed stream F
4 rectification column
6 rectifying section
8 stripping section
10 stream C
12 absorption column
14 first cooling loop
16 second cooling loop
18 first chimney tray
20 side take-off
22 bottom space
24 third cooling loop
26 air cooler
28, 30, 38, 40, streams
32 second chimney tray
34 third chimney tray
36 temperature sensor
44 stripping unit
100 abscissa; time in months
102 ordinate; runtime in days and temperature in degrees Celsius
103 secondary ordinate; amount of polymer in tons
104 measured values; temperature in ° C.
106 measured values; polymer in tons
108 measured values; runtime in days
110 abscissa; time in months
112 ordinate; runtime in days, temperature in ° C. and glyoxal concentration in weight ppm
113 secondary ordinate; amount of polymer in tons
114 measured values; temperature in ° C.
116 measured values; amount of polymer in tons
117 measured values; glyoxal concentration in weight ppm
118 measured values; runtime in days
120 abscissa; temperature in ° C.

The invention claimed is:

1. A process for production of acrylic acid comprising:
 a) preparing a product gas mixture by a catalytic gas-phase oxidation of at least one $C_3$ precursor compound to obtain the product gas mixture comprising acrylic acid and glyoxal;
 b) cooling the product gas mixture;
 c) contacting the cooled product gas mixture in an absorption column comprising at least two cooling loops in countercurrent with an absorbent to obtain an absorbate A, comprising the absorbent and absorbed acrylic acid;
 d) condensing a high boiler fraction of the product gas mixture in a first cooling loop of the at least two cooling loops;
 e) condensing a low boiler fraction of the product gas mixture in a second cooling loop of the at least two cooling loops;
 f) maintaining a temperature of the absorbate A in the second cooling loop at a value of at least 56° C.;
 g) removing an acid water stream comprising glyoxal from the absorption column at a side take-off located above the second cooling loop;
 h) removing a stream F of absorbate A from the absorption column at a side take-off, located at the first cooling loop or at a height of the absorption column between the first cooling loop and the second cooling loop;
 i) transferring at least part of the absorbate A removed from the absorption column in h) into a rectification column comprising a rectifying section and a stripping section;
 j) enriching the absorbent in the stripping section and enriching acrylic acid in the rectifying section;
 k) withdrawing a stream C of crude acrylic acid comprising at least 90% by weight of acrylic acid out of the rectifying section as a side stream.

2. The process according claim 1, wherein the cooling in step b) is carried out as direct cooling of the product gas mixture with a finely sprayed cooling liquid, wherein a portion of the cooling liquid evaporates.

3. The process according to claim 2, wherein the absorption column comprises a bottom space, from which a first portion of a bottom liquid, comprising the absorbent, is withdrawn and applied in the direct cooling as the cooling liquid.

4. The process according to claim 3, wherein a second portion of the bottom liquid is fed to a distillation unit comprising a distillation column and a circulation heat exchanger.

5. The process according to claim 4, wherein in the distillation column, the bottom liquid of the absorption column fed to the distillation unit is separated by distillation into a vapor, in which the proportion by weight of absorbent is greater than the proportion by weight of absorbent in the bottom liquid of the absorption column, and into a liquid concentrate, in which the proportion by weight of constituents with higher boiling point than the absorbent, under distillation conditions, is greater than the proportion by weight of these constituents in the bottom liquid of the absorption column.

6. The process according to claim 3, wherein the second cooling loop is in a second position counting all cooling loops present in the absorption column from the bottom space of the absorption column upwards.

7. The process according to claim 1, wherein the absorption column comprises three cooling loops and a third cooling loop is arranged above the first cooling loop and the second cooling loop.

8. The process according to claim 1, wherein the second cooling loop is arranged above the first cooling loop, the first cooling loop comprises a first chimney trail and the product gas mixture is fed into the absorption column below the first chimney trail.

9. The process according to claim 1, wherein the second cool g loop comprises an air cooler.

10. The process according to claim 1, wherein low boilers are stripped out of the absorbate A in a stripping unit between step c) and step d).

11. The process according to claim 1, wherein part of the absorbent, which is withdrawn from the stripping section of the rectification column is recycled into the absorption column.

12. The process according to claim 1, wherein the boiling point of the absorbent at standard pressure is at least 50° C. above the boiling point of acrylic acid at the same pressure.

13. The process according to claim 1, wherein the absorbent is a mixture of 75% to 99.9% by weight of a first constituent, the first constituent consisting of 70% to 75% by weight of diphenyl ether and 25% to 30% by weight diphenyl, and 0.1% to by weight of dimethyl phthalate.

14. The process according to claim 1, wherein the at least one $C_3$ precursor compound is propylene, glycerol and/or acrolein.

15. The process according to claim 14, wherein the propylene as the $C_3$ precursor compound is obtained by a partial dehydrogenation and/or oxydehydrogenation of propane preceding the catalytic gas phase oxidation.

* * * * *